United States Patent [19]
Hock et al.

[11] Patent Number: 5,888,753
[45] Date of Patent: Mar. 30, 1999

[54] MONOCLONAL ANTIBODIES AGAINST THE PLASMIN-ANTIPLASMIN COMPLEX, A METHOD FOR THE PREPARATION THEREOF AND THE USE THEREOF

[75] Inventors: Johann Hock, Marburg, Germany; Hermann Pelzer, Miami, Fla.

[73] Assignee: Behring Diagnostics GmbH, Marburg, Germany

[21] Appl. No.: 882,978

[22] Filed: May 14, 1992

[30] Foreign Application Priority Data

May 16, 1991 [DE] Germany .......................... 41 15 993.4

[51] Int. Cl.$^6$ .......................... G01N 33/53; C07K 16/36
[52] U.S. Cl. .................. 435/7.92; 435/337; 435/217; 530/388.25; 530/389.3; 530/391.1; 530/391.3; 436/518; 436/69; 436/548
[58] Field of Search .............................. 435/7.92, 240.27, 435/217, 337; 436/518, 548, 69; 530/388.25, 389.3, 391.1, 391.3

[56] References Cited

U.S. PATENT DOCUMENTS 4,216,291  8/1980  Collen .......................................... 435/7

FOREIGN PATENT DOCUMENTS

A-896 543    8/1983   Belgium .
A-0159025   10/1985   European Pat. Off. .

OTHER PUBLICATIONS

Paul Holvoet et al, An Enzyme–Linked Immunosorbent Assay (ELISA) for the Measurement of Plasmin–$\alpha 2$–Antiplasmin Complex in Human Plasma–Application to the Detection of In Vivo Activation of the Fibrinolytic System; Thrombosis and Haemostasis 56, pp. 124–127 (1986).

Jun Mimuro et al, Monoclonal Antibodies to Discrete Regions in Plasmin Inhibitor; Blood, vol. 69, No. 2, pp. 446–453 (1987).

G. Koehler et al, Continuous cultures of fused cells secreting antibody of predefined specificity; Nature, vol. 256, pp. 495–497 (1975).

Monoclonal Antibodies, Appendix pp. 363–374 Kennett, R.et.al., eds. Plenum Press, 1980.

Melchers, F., Potter, M. and Warner, N., Current Topics in Microbiology and Immunology, Preface vol. 81, Springer Verlag (1978).

Harpel, J. Clin. Invest., 68:46–55 (1981).

Harlow et al ed. 1988 Antibodies A Laboratory Manual, Cold Spring Harbor Laboratory pp. 555,556,558,561,612.

Harlow et al *Antibodies, A Laboratory Manual* , 1988 Cold Spring Harbor Laboratory pp. 141–142.

Proceedings of the National Academy of Sciences of USA, 8d. 87, Feb. 1990; Reed et al.; Synergistic Fibrinolysis: Combined Effects of Plasminogen Activators and an Antibody that Inhibits Alpha 2–Antiplasmin. pp. 1114–1118.

*Primary Examiner*—Frank C. Eisenschenk
*Attorney, Agent, or Firm*—Finnegan, Henderson, Farabow, Garrett & Dunner, L.L.P.

[57] ABSTRACT

The invention relates to monoclonal antibodies (MAbs) and fragments thereof which have a specific affinity for the plasmin-antiplasmin complex and which display no affinity or only a very low affinity for the individual components of these complexes, and to antigens which can be defined and/or isolated with the aid of these antibodies or antibody fragments. The antibodies, antibody fragments and antigens can be used as diagnostic aid, active substance or active substance carrier.

13 Claims, No Drawings

MONOCLONAL ANTIBODIES AGAINST THE PLASMIN-ANTIPLASMIN COMPLEX, A METHOD FOR THE PREPARATION THEREOF AND THE USE THEREOF

The invention relates to monoclonal antibodies (MAbs) and fragments thereof which have a specific affinity for the plasmin-antiplasmin (Pl-AP) complex and which display no affinity or only a very low affinity for the individual free components of this complex, and to the use thereof in diagnostic aids, as active substance or active substance carrier, and to hybridoma cell lines which produce such antibodies.

The fibrinolytic system composed of plasminogen, plasminogen activators and inhibitors thereof plays an important part inter alia in the breaking up of blood clots. The final product of a cascade-like activation chain is the serine protease plasmin which is able to cleave insoluble fibrin clots into soluble fibrin degradation products and thus prevents excessive thrombus formation. The action of plasmin is controlled by the protease inhibitor α2-antiplasmin which reacts with plasmin to form a covalent enzyme-inhibitor complex and thus inactivates plasmin. The concentration of this complex in the plasma provides information on the extent of activation of the fibrinolytic system and is therefore suitable for discovering disturbances of this system.

Determination of the concentration of the complex with a sandwich ELISA is known, wherein a first ("trapping") antibody against α2-antiplasmin functions as coating antibody, while a second, enzyme-labeled antibody against plasmin is used to detect the complex bound to the trapping antibody (Harpel, PC (1981) J. Clin. Invest. 68: 46–55; Holvoet, P et al. (1986) Thromb. Haemostas. 56:124–127). Another method for determining the plasmin-α2-antiplasmin complex with an immobilized monoclonal trapping antibody against plasminogen and with a peroxidase-labeled detection antibody against α2-antiplasmin has likewise been described (Mimuro et al. (1987) Blood 69: 446–453).

The disadvantage of the said assay systems is that the enzyme-inhibitor complex competes with the free inhibitor or proenzyme, which is normally present in the sample in large excess, for binding to the trapping antibody. The consequence is that the amount of the bound, and thus available for determination, complex depends on the concentration of the components of the complex in the sample. A solution of this problem is achieved in all the described methods by highly diluting the samples employed for the assay. This necessarily entails a considerable loss of sensitivity of the assay (see also Table 2).

Although the general method for preparing monoclonal antibodies has been known since 1975 (KöHLER and MILSTEIN, Nature, Vol. 256, p. 495 (1975)), there have still been great difficulties in producing an antibody which has the required properties, that is to say which selectively recognizes the Pl-AP complex. Crucial for the utilizability of an antibody of this type in a specific diagnostic method or as therapeutic is a low or, if possible, absent affinity for plasminogen or antiplasmin in the uncomplexed state.

The object of the invention was therefore to provide a monospecific antibody which selectively has a specific affinity for the plasmin-antiplasmin complex but no affinity or only a very low affinity for the individual components or precursors plasminogen and antiplasmin in the uncomplexed state.

It has been found, surprisingly, that it was possible to obtain antibodies of the required specificity by immunization both with plasmin and with α2-antiplasmin which has been liberated from a complex with plasmin with the aid of ammonia.

The invention thus relates to monospecific antibodies against the plasmin-antiplasmin complex, which have a high specific affinity for the complex and no affinity or only a very low affinity for the individual free components.

Preferred in this connection is a monospecific antibody as described above which is produced by the hybridoma cell line BW PAP6.

The invention further relates to monospecific antibodies as described above which bind to an antigen which is bound by the reference antibody BMA PAP6.

The MAb BMA PAP6 is particularly preferred.

The invention further relates to an antigen which is bound by one of the antibodies described above.

The invention further relates to hybridoma cell lines which produce monoclonal antibodies as described above.

Preferred in this connection are hybridoma cell lines which produce the MAb BMA PAP6.

The hybridoma cell line BW PAP 6 is particularly preferred.

The invention also relates to the use of an antibody as described above for diagnosis.

The invention additionally relates to diagnostic methods for the detection of the plasmin-antiplasmin complex, wherein at least one of the antibodies described above is employed as specific binding partner.

Preferred in this connection are methods as described above, wherein at least one of the specific binding partners is provided with a detectable label.

A diagnostic method of this type wherein the label is, for example, an enzyme, and the other specific binding partner is bound directly or indirectly to a solid phase, is particularly preferred.

By plasmin-antiplasmin complex is meant within the meaning of this invention all plasmin-antiplasmin complexes which can be detected by the antibodies according to the invention.

The antibodies according to the invention allow the construction of assays for the quantitative determination of the concentration of the Pl-AP complex, for example in undiluted plasma samples, irrespective of the concentrations of free plasminogen and α2-antiplasmin in the sample. The antibodies according to the invention can be poly- or monoclonal, and monoclonal antibodies are preferred. The use of polyclonal antibodies which have been purified by methods known to the person skilled in—the art is also possible.

Antibodies within the meaning of the invention are also the immunoreactive fragments, known per se to the person skilled in the art, of antibodies. Preferred fragments in this connection are F(ab')2 fragments.

A preferred antibody within the meaning of this invention is BMA PAP 6, which is produced by the hybridoma cell line BW PAP 6. This hybridoma cell line was deposited under the number DSM ACC2004 on Feb. 21, 1991, at the Deutsche Sammlung von Mikroorganismen und Zellkulturen GmbH (DSM), Mascheroder Weg 1b, D-3300 Braunschweig, Federal Republic of Germany.

This cell line was obtained, for example, by methods known to the person skilled in the art (see, for example, Monoclonal Antibodies, Kennett, R.: McKearn, T. and Bechtol, K.; eds., Plenum Press, 1980, including the literature contained therein), by hybridization of a mouse myeloma cell line with spleen cells from mice which have been immunized with plasmin or α2-antiplasmin which has been liberated from a Pl-AP complex with the aid of ammonia, preferably 0.1–1% (v/v). Various murine (mouse) myeloma cell lines can be used for the fusion. Some of these cell lines are described in MELCHERS, F.; POTTER, M. and WARNER, N., eds.; Current Topics in Microbiology and Immunology, Vol. 81, Springer Verlag (1978). The hybridization is usually carried out in the presence of polyethylene glycol as fusion promoter, but other fusion promoters such as sendai virus can also be used. The ratio of spleen to myeloma cells may vary, and a ratio of 2–10:1 is normally used. After the fusion, the cells are cultivated by known methods, and the cell supernatants are assayed for the presence of antibodies with the required properties. It is possible to employ for this, for example, an enzyme immunoassay wherein a microtiter plate coated with anti-mouse IgG (from rabbits) is incubated with cell supernatants.

This is followed by incubation a) with a standard human plasma and b) with a plasma rich in Pl-AP complex. In a further incubation step, a mixture of peroxidase-labeled antibodies against plasmin and antiplasmin is added, and subsequently the bound peroxidase activity is determined. It is possible where appropriate to carry out washing steps between the incubation steps. Cell supernatants which react with b) but not with a) contain antibodies with the required properties, and the corresponding cell cultures are used for further cloning.

Larger amounts of the required antibodies according to the invention can be obtained, for example, by in vitro (cell cultures) or in vivo (ascites) culturing. The antibodies obtained in this way can be characterized by their immunoglobulin class and subclass and, for example, by their electrophoretic behavior.

Antibodies are preferably employed in diagnosis in the heterogeneous or homogeneous immunochemical determination methods known per se to a person skilled in the art, with particle-enhanced nephelometry or turbidimetry being preferred for the homogeneous methods. In the heterogeneous immunoassays the solid phase-bound sandwich assay is preferred, in which case the solid phase is preferably a polystyrene tube, a microtiter plate, a latex particle, a magnetizable particle or a sheet-like solid phase. The solid phase-bound sandwich assay is particularly preferred, with a microtiter plate being employed as solid phase.

A diagnostic method for the detection of plasmin-antiplasmin complex is also preferred, wherein at least one antibody according to the invention is employed as specific binding partner.

The second specific binding partner can be another antibody or an antibody fragment, a lectin or a receptor. Preferred in this connection is a method in which the second specific binding partner is also a monoclonal antibody according to the invention which recognizes an epitope other than that recognized by the first specific binding partner; this makes it possible to construct one-step assays.

If the binding reaction is followed by a washing step in which the complex bound to the trapping antibody is removed from the liquid supernatant, it is also possible to employ as second specific binding partner an antibody against one of the individual components of the complex; this can also be polyclonal.

One of the specific binding partners can carry a label for detection and for quantification. This label is known per se to the person skilled in the art and can be, for example, a chromophore, a luminophore, a fluorophore, an enzyme, a radioactive isotope or a colored or uncolored particle. Methods preferred for the preparation of antibody-coated solid phases are those which bind the unlabeled specific binding partner by methods known per se to the person skilled in the art directly or indirectly, for example via another antibody or a biotin-avidin bridge which is coupled to a solid phase.

Biosensors which are employed to detect proteins using a specific antibody are known per se to the person skilled in the art. The antibodies according to the invention can also be employed in such biosensors.

The antibodies according to the invention can also be, for example, radiolabeled by methods known to the person skilled in the art in order to employ them for immunoscintigraphy.

The embodiments described in the example are particularly preferred.

The example and claims form part of the disclosure.

The following example explains the invention but does not restrict it in any way:

EXAMPLE 1

Step 1: Preparation of plasmin-inactivated α2-antiplasmin 2.3 mg of α2-antiplasmin (from Biopool) in 1.2 ml of buffer A (0.1 mol/L KH2PO4, 0.15 mol/L NaCl) were loaded onto plasmin-Fractogel (24 mg of plasmin—from Kabi—coupled to 4 ml of CNBr-Fractogel$^R$) and incubated at 25° C. for 1 h in order to allow formation of a P1-AP complex. The gel was washed with 40 ml of buffer A. Subsequently the gel was washed with 0.25% ammonia in order to hydrolyze the linkage, which is unstable to nucleophilic agents, between enzyme and inhibitor. The protein-containing fractions of the ammonia eluate contained 1.3 mg of plasmin-inactivated α2-antiplasmin.

Step 2: Preparation and purification of monoclonal antibodies against Pl-AP 2.1. Obtaining antibody-producing cells BALB/c mice were immunized by subcutaneous injection of an emulsion of 50 μg of plasmin in complete Freund's adjuvant (day 1). 50 μg of plasmin emulsified in incomplete Freund's adjuvant were likewise injected subcutaneously on each of days 28 and 56. An intraperitoneal injection of 100 μg of plasmin in 0.5 ml of physiological saline followed on day 92. On day 95, after removal of the spleen, lymphocytes were obtained by mechanical disintegration. Lymphocytes were obtained in the same way from animals which had been immunized with plasmin-inactivated α2-antiplasmin (prepared as described in Step 1).

2.2. Fusion of lymphocytes with myeloma cells

Hybridoma cells were obtained by standard methods (Kohler and Milstein, 1975; Nature 256: 495–497): the myeloma cell line SP2/0-Ag14 was cultivated in Dulbecco's modified Eagle's medium (DMEM) with 10% fetal calf serum (FCS). The spleen cells from a mouse (about 108 lymphocytes) were mixed with 5×107 myeloma cells, washed in serum-free DMEM and spun down. After complete removal of the supernatant, 0.5 ml of a 50% strength solution of polyethylene glycol 4000 in DMEM was added dropwise over the course of one minute to the cell pellet. The suspension was incubated at 37° C. for 90 seconds and subsequently diluted by addition of 7.5 ml of DMEN over a period of 5 minutes. After incubation at room temperature for 10 minutes, the mixture was made up to 40 ml with DMEM, and the cells were spun down. The supernatant was aspirated off and then the cells were resuspended in DMEM containing 20% FCS and inoculated onto 6 microtiter plates (200 μl per cavity). Hybridoma cells were selected by addition of 13.6 mg/ml hypoxanthine, 0.18 mg/ml aminopterin, 3.9 mg/ml thymidine (HAT medium). Used medium was replaced at intervals of 3–4 days by fresh medium, and HAT medium was replaced by HT medium after 10 days.

2.3 Assay for Pl-AP antibodies 14 days after the fusion, the cell culture supernatants were assayed by enzyme immunoassay for antibodies against the Pl-AP complex. Polystyrene microassay plates were incubated with 3 µg/ml rabbit anti-mouse IgG in 0.1 mol/L NaHCO3, pH 9.6 (24 h, 4° C.). Subsequently cell culture supernatants were applied (2 h, 37° C.), followed by incubation with standard human plasma (diluted 1:2). This was followed by incubation (2 h, 37° C.) with a mixture of peroxidase-labeled antibodies from rabbits against plasminogen and α2-antiplasmin (each 1 µg/ml). The substrate used was a solution of 0.1% (weight/volume) of 2,2'-azinodi (3-ethylbenzothiazoline-6-sulfonate) and 0.012% (volume/volume) of H2O2 in 0.1 mol/L citric acid, 0.1 mol/L Na2HPO4, pH 4.5. After incubation at 37° C. for 30 min, the absorption at 405 nm was measured. Washing was carried out between the individual incubation steps with 0.01 mol/L Na2HPO4, 0.01 mol/L NaH2PO4, pH 7.2, 0.15 mol/L NaCl, 0.05% Tween 20 (PBS/Tween). All the reagents were diluted in PBS/Tween with 2% bovine serum albumin. In parallel, an enzyme immunoassay was carried out with the same cell culture supernatants, employing in place of standard human plasma a plasma with a high content of Pl-AP complex (obtained by incubation of standard human plasma with immobilized urokinase). Antibodies which react with the Pl-AP complex (reaction with Pl-AP-containing plasma) but do not recognize free plasminogen or α2-antiplasmin in plasma (no reaction with standard human plasma) are particularly suitable for use in an ELISA for the Pl-AP complex.

2.4. Cloning of antibody-producing cell lines

Cells whose supernatants showed a positive reaction in the assay for Pl-AP-specific antibodies were cloned by the limiting dilution method. For this, about 60 cells in DMEM containing 20% FCS and 5% human endothelial culture supernatant (Costar) were distributed over 96 cavities of a cell culture plate. Individual clones were identified microscopically and assayed for antibody production as described above. The cloning was repeated twice.

2.5. Purification of monoclonal antibodies

Clonal cell lines were transferred into roller bottles for production of antibodies and cultivated in Iscove's modified Dulbeccols medium. Cell supernatant was obtained by centrifugation and concentrated about 10-fold by ultrafiltration. The concentrate was loaded onto protein A-Sepharose-CL-4B (Pharmacia), and bound IgG was eluted with 0.2 mol/L glycine/HCl, pH 3.0. The protein-containing fractions were dialyzed against 0.1 mol/L citrate, pH 6.5, and concentrated to about 5 mg/ml by ultrafiltration Step 3: Assays on the purified antibodies 3.1. Preparation of antibody-coated polystyrene microtiter plates:

The Pl-AP specific antibodies obtained as in step 2.5. were diluted with sodium phosphate buffer solution (0.01 mol/L, pH 6.8) to a concentration of 5 µg/ml and immobilized on microtiter plates by adsorption. 150 µl of antibody solution per well were incubated at 20° C. for 20 hours, and then the liquid was aspirated off, and the plates were stored sealed air-tight at 4° C.

3.2. Procedure for the enzyme immunoassay (ELISA)

The samples to be assayed were diluted 1+1 with incubation buffer (0.1 mol/L NaCl, 0.1 mol/L tris, 1% Tween 20, 0.1% NaN3, pH 7.2). 100 µl were placed in each well and incubated at 37° C. for 30 min. The incubation solution was then removed, and the wells were washed twice with 150 µl of washing solution (0.02 mol/L sodium phosphate, 0.05% Tween 20, pH 7.6) each time. Subsequently 100 µl of peroxidase-conjugated rabbit anti-plasminogen antibodies were added to each well and incubated at 37° C. for 30 min. Removal of the conjugate solution and two washes were followed by addition of 100 µl of substrate solution (hydrogen peroxide; o-phenylenediamine) and incubation of the plate at room temperature. After incubation for 30 min, the peroxidase was inactivated with 0.1 mol/L sulfuric acid, and the extinction of the reaction solution at 492 nm was determined. Table 1 shows the absorption values (OD 492 nm/30 min) for different concentration of PL-AP complex. Both a monoclonal antibody against a Pl-AP neoantigen (PAP 6) and a monoclonal antibody against α2-antiplasmin (APl2) were employed as coating antibodies. Table 1 shows the extinctions and the measured concentrations:

TABLE 1

| Pl-AP complex (ng/ml) | Coating antibody | |
| --- | --- | --- |
| | PAP 6 OD 492 nm | APl 2 OD 492 nm |
| 3 | 0.060 | 0.040 |
| 10 | 0.066 | 0.040 |
| 30 | 0.102 | 0.060 |
| 100 | 0.211 | 0.120 |
| 300 | 0.490 | 0.300 |
| 1000 | 1.049 | 0.715 |
| 3000 | 1.678 | 1.375 |

The results show that it is possible in principle to use both antibodies against a Pl-AP neoantigen and antibodies against α2-antiplasmin as coating antibodies for the determination of Pl-AP complex.

3.3 Recovery of Pl-AP complex in plasma

Defined amounts of Pl-AP complex were added to a plasma sample (normal plasma) and determined by ELISA. Both PAP 6 and APl 2 were employed as coating antibodies for plates. The absorptions are shown in Table 2:

TABLE 2

| Pl-AP complex (ng/ml) | Coating antibodies | |
| --- | --- | --- |
| | PAP 6 OD 492 nm | APl 2 OD 492 nm |
| 30 | 0.033 | 0.003 |
| 100 | 0.086 | 0.004 |
| 300 | 0.237 | 0.013 |

The results show unambiguously that Pl-AP is detectable in the plasma sample diluted 1:2 using the trapping antibody PAP 6 which is directed against a neoantigen on the Pl-AP complex, whereas Pl-AP can be found only in high concentrations using the trappin antibody APl 2 (directed against α2-antiplasmin) because of the competition of free α2-antiplasmin and Pl-AP complex.

3.4 Detection of Pl-AP complex in plasma

Plasma was mixed with urokinase and incubated at 37° C. for 180 min. Aliquots were removed at various times, and the reaction was stopped by addition of aprotinin. The samples were diluted 1+99 with PBS/aprotinin and assayed by ELISA. The monoclonal antibody BMA PAP6 (against Pl-AP neoantigen) was used for coating the microtiter plates. Table 3 hows the results.

TABLE 3

| Time (min) | OD 492 nm |
|---|---|
| 0 | <0.1 |
| 15 | 0.1 |
| 30 | 0.18 |
| 60 | 0.24 |
| 120 | 0.37 |
| 180 | 0.56 |

The results show that the concentration of the Pl-AP complex in the plasma increases with time during the course of plasminogen activation by urokinase.

We claim:

1. Monoclonal antibodies against the plasmin-antiplasmin complex, which has a high specific affinity for the complex and essentially no affinity for the individual free components or precursors plasminogen and antiplasmin.

2. A monoclonal antibody as claimed in claim 1, which is produced by the hybridora cell lines BW PAP6.

3. A monoclonal antibody as claimed in claim 1, which binds to an antigen which is bound by the antibody BMA PAP6.

4. A monoclonal antibody as claimed in claim 1, which is the MAb BMA PAP6.

5. An epitope which is bound by a monoclonal antibody as claimed in claim 1.

6. A hybridoma cell line which produces a monoclonal antibody as claimed in claim 1.

7. A hybridoma cell line which produces the MAb BMA PAP6.

8. A hybridoma cell line which is the BW PAP 6 cell line.

9. An immunochemical method for the detection and determination of plasmin-antiplasmin complex (papc) in a sample of a biological fluid, comprising the steps of (i) incubating the sample of a biological fluid with the monoclonal antibody of claim 1; and (ii) determining the amount of antibody/papc complex formed in the sample.

10. The method of claim 9, wherein a second antibody
specific for an epitope of the plasmin-antiplasmin complex different from that recognized by the monoclonal antibody, or
specific for plasmin or antiplasmin is bound to the complex of step (ii).

11. The method of claim 10, wherein at least one of the antibodies is provided with a label.

12. The method of claim 11, wherein the unlabelled antibody is bound directly or indirectly to a solid phase.

13. The method of claim 11, wherein the label is an enzyme.

* * * * *